United States Patent
Jeremias et al.

(10) Patent No.: US 10,131,612 B2
(45) Date of Patent: Nov. 20, 2018

(54) METHOD FOR THE PRODUCTION OF AN ADSORBENT MADE OF METAL-ORGANIC FRAMEWORK STRUCTURES (MOF)

(71) Applicant: FRAUNHOFER-GESELLSCHAFT ZUR FÖRDERUNG DER ANGEWANDTEN FORSCHUNG E.V., München (DE)

(72) Inventors: Felix Jeremias, Freiburg (DE); Stefan Henninger, Endingen (DE)

(73) Assignee: Fraunhofer-Gesellschaft zur förderung der angewandten Forschung e.V., München (DE)

( * ) Notice: Subject to any disclaimer, the term of this patent is extended or adjusted under 35 U.S.C. 154(b) by 0 days.

(21) Appl. No.: 15/502,025

(22) PCT Filed: Jun. 24, 2015

(86) PCT No.: PCT/EP2015/064189
§ 371 (c)(1),
(2) Date: Feb. 6, 2017

(87) PCT Pub. No.: WO2016/020104
PCT Pub. Date: Feb. 11, 2016

(65) Prior Publication Data
US 2017/0226040 A1    Aug. 10, 2017

(30) Foreign Application Priority Data
Aug. 6, 2014 (DE) .................. 10 2014 215 568

(51) Int. Cl.
*B01J 20/22* (2006.01)
*C07C 51/41* (2006.01)
*C07F 19/00* (2006.01)
*C07C 63/307* (2006.01)

(52) U.S. Cl.
CPC ........... *C07C 51/418* (2013.01); *B01J 20/226* (2013.01); *C07C 63/307* (2013.01); *C07F 19/005* (2013.01)

(58) Field of Classification Search
CPC ...... B01J 20/22; C07C 51/418; C07C 63/307; C07F 19/005
USPC ....................................................... 502/401
See application file for complete search history.

(56) References Cited

U.S. PATENT DOCUMENTS 9,474,997 B1 * 10/2016 Peterson ................ B01D 53/04
2009/0227446 A1    9/2009 Chang et al.
2010/0226991 A1    9/2010 Horcajada-Cortes et al.

FOREIGN PATENT DOCUMENTS

| WO | WO 2005/049484 A1 | 6/2005 |
| WO | WO 2007/014678 A1 | 2/2007 |
| WO | WO 2007/118841 A2 | 10/2007 |
| WO | WO 2013/004726 A1 | 1/2013 |
| WO | WO 2014/012989 A1 | 1/2014 |

OTHER PUBLICATIONS

Jeremias, "Synthesis and Characterization of metal-organic Frameworks for Heat Transformation Applications", *Heinrich Heine Universität Düsseldorf*, Dissertation, 1-61 (2014).
European Patent Office, International Search Report and Written Opinion in International Application No. PCT/EP2015/064189 (dated Oct. 7, 2015) 23 pp.
International Bureau of WIPO, International Preliminary Report on Patentability in International Application No. PCT/EP2015/064189 (dated Feb. 16, 2017) 10 pp.
Jeremias, "Synthesis and Characterization of metal-organic Frameworks for Heat Transformation Applications", *Heinrich Heine Universität Düsseldorf*, Dissertation, Introduction, pp. 1-61 (Published Feb. 27, 2015) http://publica.fraunhofer.de/dokumente/N-328221.html Volltext urn:nbn:de:0011-n-3282213.
Jeremias, "Synthesis and Characterization of metal-organic Frameworks for Heat Transformation Applications" to obtain a doctoral degree from the Faculty of Mathematics and Natural Sciences at Heinrich Heine University, Düsseldorf (242 pgs—Feb. 27, 2015) http://publica.fraunhofer.de/dokumente/N-328221.html Volltext urn:nbn:de:0011-n-3282213.

* cited by examiner

*Primary Examiner* — Edward M Johnson
(74) *Attorney, Agent, or Firm* — Leydig, Voit & Mayer, Ltd.

(57) ABSTRACT

The present invention relates to a method for the production of an absorbent made of metal-organic framework structures (MOF), in the case of which at least one metal salt is converted with at least one organic ligand. The conversion is effected at a temperature greater than 100° C. in a solvent mixture which comprises DMSO and water. The invention relates in addition to an absorbent produced with the method according to the invention or to a substrate coated with such an adsorbent and also to possibilities of use of such an adsorbent or substrate.

13 Claims, No Drawings

METHOD FOR THE PRODUCTION OF AN ADSORBENT MADE OF METAL-ORGANIC FRAMEWORK STRUCTURES (MOF)

CROSS-REFERENCE TO RELATED APPLICATIONS

This patent application is the U.S. national phase of International Application No. PCT/EP2015/064189, filed on Jun. 24, 2015, which claims the benefit of German Patent Application No. 10 2014 215 568.1, filed Aug. 6, 2014, the disclosures of which are incorporated herein by reference in their entireties for all purposes.

The present invention relates to a method for the production of an absorbent made of metal-organic framework structures (MOF), in the case of which at least one metal salt is converted with at least one organic ligand. The conversion is effected at a temperature greater than 100° C. in a solvent mixture which comprises DMSO and water. In addition, the invention relates to an absorbent produced with the method according to the invention or to a substrate coated with such an absorbent and also to possibilities of use of such an absorbent or substrate.

Metal-organic network connections (metal-organic frameworks, MOFs) are included in microporous materials. On a molecular level, they consist of cationic metal ion clusters (Secondary Building Units, SBUs) which are bridged by organic anions (linkers) forming polyvalent coordinative bonds. Because of the highly symmetrical, crystalline construction of the lattice structures and the fact that the porosity is produced in fact at a molecular level, MOFs are included in general in materials with the greatest inner surface (up to $S_{BET}>4,000$ m$^2$/g) and, because of their chemical variety, they are of great interest for applications such as gas storage, catalysis, sorption heat transformation and many more where they can supplement or replace materials, such as silica gels, zeolites or activated carbons. Because of the numerous combination possibilities of SBUs and clusters, many thousands of structures are in fact known.

MOFs are produced artificially, there are various possibilities for this. It is common to all of them that metal cations and linker anions are made to react and in fact in such a slow and controlled manner that the desired crystalline phase can be formed. Apart from a few exceptions (anodic synthesis or galvanic displacement), the metal cations (in the form of a readily soluble metal salt) are thereby present in a high concentration. The anions are produced in a low concentration in situ from the corresponding free acid (likewise present) by means of deprotonation in order to achieve a slow, controlled crystal formation.

The deprotonation can be achieved by several methods, for instance by the addition of a basic compound, cathodically by reduction or, as standard, by solvothermal syntheses, the deprotonation being effected by heating (equilibrium displacement or formation of basic decomposition products of the solvent). Most MOFs to date have been able to be produced only by solvothermal synthesis.

Solvents used frequently in the state of the art are, in pure form or as a mixture, dialkyl formamides, low alcohols and water (i.e.: "hydrothermal synthesis"). According to the MOF used, only a few solvents thereby lead to the formation of the desired structure. In the case of the wrong choice of solvent, an amorphous, non-porous or even no product at all is then obtained. Numerous MOFs, in particular highly-porous MIL structures which are intended to be used as sorption material for heat transformation applications, can be produced, according to the state of the art, only when using water as solvent.

In US 2010/0226991 A1, a hydrothermal synthesis at 100° C. is described. The reaction could hence be implemented theoretically at atmospheric pressure and in an open apparatus, even if it is not proposed in US 2010/0226991 A1 for this purpose. A suspension of trimesic acid in aqueous solution of FeCl$_3$.6 H$_2$O serves as reaction mixture. This synthesis provides MOFs with low crystallinity and a small inner surface. Since the process takes place in suspension, the MOFs are obtained as a mixture with unconverted linker compound. Complex cleaning is therefore necessary. In addition, this synthesis is not suitable for coating methods since particles of the linker compound are incorporated without control in the layer, as a result of which undesired material properties are produced.

In addition, US 2010/0226991 A1 describes a hydrothermal synthesis at 130° C. with the addition of hydrofluoric acid, the Fe$^{3+}$ cations being prepared in situ from metallic iron and nitric acid. However, this synthesis must be implemented at high pressure in an autoclave.

In US 2009/0227446 A1, a hydrothermal synthesis with a similar reaction mixture with microwave radiation at 200° C. is described. This must also be implemented at high pressure and in a closed reaction vessel.

Considered as a whole, the synthesis methods described in the state of the art have the following disadvantages:

Because of the typical reaction temperatures (>100° C.), the process must take place at high pressure and in corresponding vessels (autoclaves). This impedes the reaction control (no view into the vessels) and increases the cost expenditure enormously, in particular if modified variants of the solvothermal synthesis are intended to be used (e.g. coatings by means of temperature gradients or cathodic deprotonation). Continuous synthesis implementation, which is desirable for reasons of economy of the process is particularly difficult to achieve in the case of syntheses at high pressure.

The compounds used as linkers, typically aromatic or olefinic di-, tri- or tetracarboxylic acids, are generally poorly water-soluble and only dissolve at temperatures >100° C. in the reaction medium. During cooling they precipitate again. The MOF isolated after conclusion of the reaction is therefore generally contaminated with unconverted radicals of the linker molecule which must be removed by complex washing with organic solvents. Simple separation of the MOF from the synthesis solution (e.g. by filtration) is likewise impossible, which likewise is an obstacle to a continuous reaction implementation.

The hydrothermal syntheses known from the state of the art for MOFs at T≤100° C. provide MOFs with comparatively low crystallinity and a small inner surface, in addition in the form of very small particles, even nanoparticles. Since the process takes place here in suspension, these MOFs are also obtained as a mixture with unconverted linker compound. Complex cleaning is therefore required. The corresponding syntheses are not suitable for coating methods because particles of the linker compound are incorporated without control in the layer, as a result of which undesired material properties are produced.

Starting from the state of the art, it is accordingly the object of the present invention to provide a method for the production of an absorbent made of metal-organic framework structures, which can be effected at atmospheric pressure and from a homogeneous solution and by means of which the difficulties of the methods described in the state of the art are overcome.

This object is achieved by the features of the adsorbent and the method for the production of the absorbent described herein, as well as the advantageous developments thereof. Uses according to the invention are also described.

According to the invention, a method for the production of an absorbent made of metal-organic framework structures (MOF) is hence provided, in the case of which at least one metal salt is converted with at least one organic ligand. The conversion is thereby effected at a temperature greater than 100° C. in a solvent mixture which comprises DMSO and water.

The method according to the invention is distinguished by a zeotropic DMSO-water mixture being used as solvent instead of water. DMSO is thereby not a common solvent used in MOF synthesis or in general in the synthesis of inorganic solids. By using a solvent comprising DMSO and water, a boiling point of the reaction mixture of above 100° C. can be achieved even at atmospheric pressure. Hence, it is possible by means of the method according to the invention to produce an MOF which is produced in a standard hydrothermal manner at atmospheric pressure. As a result, costs are saved since high-pressure-resistant apparatus is not required. Furthermore, the solvent mixture comprising DMSO and water which is used is an excellent solvent for most metal salts and organic compounds, as a result of which the reaction mixture is present in the form of a homogeneous solution. As a result, the implementation of a large-scale, even continuous, production is significantly easier because any resulting MOF can be removed by filtration from the process during operation since it ultimately concerns the single solid suspended in the solution.

As a result of the fact that the method can be implemented at atmospheric pressure and from a homogeneous solution, continuous synthesis implementation is hence possible, as a result of which the method according to the invention can be implemented in a significantly more economical manner than the methods known from the state of the art.

The use of water in the method according to the invention is necessary since the MOFs to be produced generally comprise water molecules even in the dehydrated state. At least a certain proportion of water must therefore be present in the reaction mixture.

With the method according to the invention, MOFs with high crystallinity and a large inner surface can be obtained. The use of a solvent mixture comprising DMSO and water is hereby crucial for success of an MOF synthesis effected at normal pressure and from a homogeneous solution. When using other solvents instead of DMSO in the solvent mixture, either merely X-ray-amorphous, non-porous structures can thus be obtained or the solution gels immediately or no solid at all is obtained. By using a solvent mixture comprising DMSO and water in the method according to the invention, MOFs with high crystallinity and a large inner surface can thus be obtained, the synthesis being able thereby to be implemented simultaneously at atmospheric pressure and from a homogeneous solution.

In a preferred variant of the method according to the invention, the solvent comprises at least one chemically reducible anion. Such a chemically reducible anion is reduced by the DMSO contained in the reaction mixture and also the decomposition products thereof. The thereby produced reduced product assists the deprotonation of the organic ligand and hence the formation of the MOF.

The chemically reducible anion is selected preferably from the group consisting of nitrate, chlorite, chlorate, perchlorate, bromite, bromate, perbromate, iodite, iodate, periodate, sulphate, hydrogen sulphate or mixtures hereof.

In a particularly preferred variant of the method according to the invention, the metal salt is a metal nitrate. If the metal salt used concerns a metal nitrate, then the nitrate is reduced, during conversion, by DMSO and also the decomposition products thereof to form nitrite which is more basic and thus assists the deprotonation of the organic ligand and hence the formation of the MOF.

DMSO and metal nitrates, according to their safety data specifications, are considered to be non-compatible chemicals. This can obviously be attributed to the fact that poorly soluble DMSO-solvated metal nitrate can be formed relatively easily, which has a potentially explosive effect. As a result of the water proportion in the reaction mixture and also the increased temperatures of the method according to the invention, the risk of an explosion is reduced. Further possibilities for minimising the risk of an explosion can be deduced from embodiment 1.

A particularly preferred variant of the method according to the invention provides that the metal is selected from the group consisting of Mg, Ca, Sr, Ba, Sc, Y, Ti, Zr, Hf, V, Nb, Cr, Mo, W, Mn, Re, Ru, Os, Fe, Co, Rh, Ir, Ni, Pd, Pt, Cu, Ag, Au, Zn, Cd, Al, Ga, In, Si, Sn, Pb, As, Sb, Bi and rare earth metals. The metal is thereby particularly preferably a transition metal. Very particularly preferably, the metal is selected from the group consisting of Fe, Zn, Cu, Co, Ru, Os, Mn, Ni and rare earth metals.

In a further preferred variant of the method according to the invention, the organic ligands have bridging oxygen-, nitrogen or sulphur atoms.

Furthermore, it is preferred that the organic ligands are selected from the group consisting of bidentate ligands, polydentate ligands and mixtures hereof.

A further preferred variant of the method according to the invention provides that the organic ligands are selected from the group consisting of dicarboxylic acids, tricarboxylic acids, imidazoles, triazoles and mixtures hereof.

Furthermore, it is preferred that the organic ligands are selected from the group consisting of trimesic acid, terephthalic acid, 4,4'-bipyridine, biphenylbisulphonic acid, 2,6-naphthalenedicarboxylic acid, fumaric acid, isophthalic acid, phthalic acid, oxalic acid and mixtures hereof.

A further preferred variant of the method according to the invention provides that the solvent mixture comprises between 1 and 50% by weight, preferably between 10 and 30% by weight, particularly preferably between 15 and 25% by weight, of water and/or between 50 and 99% by weight, preferably between 70 and 90% by weight, particularly preferably between 75 and 85% by weight, of DMSO. The sum of the proportions by percentage weight of DMSO and water in the solvent mixture is hereby preferably 100% by weight. The percentage proportion of DMSO and water in the solvent mixture has an influence on the boiling point of the solvent mixture. The desired boiling point of the solvent mixture can thus be adjusted by choice of the corresponding proportions of DMSO and water in the solvent mixture. For example, at a proportion of 20% by weight of water and 80% by weight of DMSO, the solvent mixture has a boiling point of 130° C. at atmospheric pressure. This solvent mixture can consequently be heated up to this temperature at atmospheric pressure in the liquid state.

In a further preferred variant of the method according to the invention, the conversion is effected with reflux and/or at a temperature of 110 to 180° C., preferably of 120 to 150° C., particularly preferably of 125 to 135° C.

Furthermore, it is preferred that the conversion is implemented at a pressure of 1 to 5 bar, preferably at atmospheric pressure. It is particularly preferred that the method according to the invention is implemented without additional application of pressure.

A further preferred variant of the method according to the invention provides that the reaction mixture comprises at least one supplement, which is selected from the group consisting of nitric acid, hydrofluoric acid, hydrochloric acid, hydrobromic acid, methane sulphonic acid, toluene sulphonic acid, sulphamic acid or sulphuric acid and mixtures hereof. Due to the presence of such supplements in the reaction mixture, the crystallinity of the obtained MOFs can be improved.

In a further preferred variant of the method according to the invention, the reaction duration is 12 to 48 h, preferably 18 to 30 h, particularly preferably 22 to 26 h.

A further preferred variant of the method according to the invention provides that the resulting adsorbent is washed. Washing is thereby preferably effected with a solvent mixture which comprises between 1 and 50% by weight, preferably between 10 and 30% by weight, particularly preferably between 15 and 25% by weight, of water and/or between 50 and 99% by weight, preferably between 70 and 90% by weight, particularly preferably between 75 and 85% by weight, of DMSO, the sum of the proportions by percentage weight of DMSO and water in the solvent mixture preferably being 100% by weight.

Furthermore, it is preferred that, after conversion, the reaction mixture is reprocessed, the solid produced during the conversion of the reaction mixture being separated, preferably being centrifuged or filtered off, from the supernatant solution.

A further preferred variant of the method according to the invention provides that at least one substrate which is to be coated with the adsorbent is immersed in the reaction mixture as cathode together with a counter-anode and subsequently the conversion is implemented, the adsorbent being deposited on the substrate in the form of a layer, and, during conversion, a voltage being applied between the electrodes which effects a current density of 200-1,000 mA/dm$^2$, particularly preferably 300 to 500 mA/dm$^2$, at the beginning of the conversion.

By means of such a combination of cathodic coating and thermal gradient method, the formation of a functional layer on substrates is possible, and in fact at high speed. The speed-determining deprotonation process of the thermal gradient method can be accelerated in this way, namely electrochemically. The following reactions hereby take place on the cathode for example:

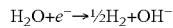

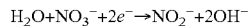

The resulting hydroxyl anions can deprotonate the organic ligands or be incorporated directly in the MOF, as a result of which crystalline layers can be produced rapidly.

Even with respect to a continuous process for the production of free, carrier-free adsorbent, the just described variant of the method according to the invention is of particular interest. Thus it is possible that the MOF formed on the cathode is continually wiped off, and merely the compounds removed from the reaction mixture need be replenished. Thus a very economical production can be achieved.

The substrate which is used is preferably electrically conductive. Particularly preferably, it concerns a substrate made of electrically conductive ceramic, electrically conductive plastic material, copper, aluminium and/or steel, very particularly preferably made of stainless steel of the types 1.4301 and/or 1.4401.

Furthermore, it is preferred that, before coating, the reaction mixture is heated without applying a voltage, this heating being effected preferably for 20 to 90 min, particularly preferably for 40 to 50 min.

In particular, the layer has a layer thickness of 120 to 180 μm, preferably 140 to 160 μm.

The present invention relates in addition to an adsorbent or to a substrate coated with an adsorbent, which is producible with the method according to the invention. An adsorbent produced with the method according to the invention or a substrate coated with an adsorbent differs consequently from products produced in the state of the art by having traces of DMSO and traces of decomposition products of DMSO which originate from the synthesis process. Such decomposition products are for example, methane thiol, formaldehyde, dimethylsulphide or dimethylsulphone.

In addition, the present invention relates to the use of an adsorbent according to the invention or of a substrate coated with adsorbent according to the invention for gas separation, gas storage, catalysis or sorption-based heat transformation.

The present invention is explained in more detail with reference to the following examples, without restricting the invention to the specially illustrated parameters.

EMBODIMENT 1

A solution of 21.25 mmol (4.48 g) of trimesic acid in 160 ml of dimethylsulphoxide was heated to 90° C. in a 250 ml three-neck flask, then a room-temperature solution of 32 mmol (12.96 g) of Fe(NO$_3$)$_3$.9H$_2$O in 32 ml of H$_2$O was added all at once with agitation. The yellow-green solution was refluxed with agitation for a duration of 24 h (internal temperature: 131° C.).

The resulting solid was centrifuged off and the supernatant solution, still hot, was tipped into 1 l of water, in order to avoid precipitation of potentially explosive Fe(NO$_3$)$_3$.6Me$_2$SO as by-product. After cleaning (washing with DMF [90° C., 5 h], ethanol [60° C., overnight] and water [90° C., 5 h]), 4.49 g of a brown-red solid was obtained. The single crystalline phase was determined by means of X-ray powder diffractometry as MIL-100.

EMBODIMENT 2

The process took place as in embodiment 1, however with reflux only for a duration of 45 min. The thus obtained, brown and slightly cloudy liquid was placed in a double-wall vessel. The outer wall was thermostatically controlled at a temperature of 45° C.

Then two sheets of 1.4301 stainless steel (1.4016 or aluminium can also be used) of the dimensions 50×50×1.5 mm were rubbed down, degreased with acetone and mounted on a specially prepared heating element, which was provided with counter-electrodes respectively at a 10 mm spacing. The blank surface of the sheets was 15 cm$^2$ per side. The test structure was immersed in the cooled original solution and the heating power was controlled (typically 210 W) such that the temperature just below the surface of the sheets to be coated was 135° C. (determined by a thermo-element inserted in a boring). Then a voltage was set, which at the start of the test effected a current intensity of 100 mA (current density: 10 A/dm$^2$). After 25 minutes, the current intensity had fallen to 50 mA, the test was ended, the introduced sheets were disassembled and placed in DMF and ethanol for respectively 24 h. The formed red-brown layer was determined by powder diffractometry as MIL-100.

The thus produced sheet is approx. 150 μm thick, stable per se, but only loosely joined to the substrate. A firmly adhering layer can be produced if for example 1.4568 stainless steel (trade name 17-7 PH®) is used as substrate.

The invention claimed is:

1. A method for the production of an absorbent made of metal-organic framework structures (MOF), wherein at least one metal salt is converted with at least one organic ligand, wherein the conversion is effected at a temperature greater than 100° C. in a solvent mixture which comprises DMSO and water;

wherein:
the metal of said one metal is selected from the group consisting of Fe, Zn, Cu, Co, Ru, Os, Mn, Ni, and rare earth metals, and
the solvent mixture comprises between 15 and 25% by weight of water and between 75 and 85% by weight of DMSO.

2. The method according to claim 1, wherein the metal salt comprises at least one chemically reducible anion selected from the group consisting of nitrate, chlorite, chlorate, perchlorate, bromite, bromate, perbromate, iodite, iodate, periodate, sulphate, hydrogen sulphate, and mixtures thereof.

3. The method according to claim 1, wherein the at least one organic ligand has bridging oxygen-, nitrogen or sulphur atom or the at least one organic ligand is selected from the group consisting of bidentate ligands, polydentate ligands, and mixtures thereof.

4. The method according to claim 1, wherein the at least one organic ligand is selected from the group consisting of dicarboxylic acids, tricarboxylic acids, imidazoles, triazoles and mixtures thereof, or the at least one organic ligand is selected from the group consisting of trimesic acid, terephthalic acid, 4,4'-bipyridine, biphenylbisulphonic acid, 2,6-naphthalenedicarboxylic acid, fumaric acid, isophthalic acid, phthalic acid, oxalic acid, and mixtures thereof.

5. The method according to claim 1, wherein the conversion is effected with reflux or at a temperature of 110 to 180° C.

6. The method according to claim 1, wherein the conversion is implemented at a pressure of 1 to 5 bar.

7. The method according to claim 1, wherein the reaction mixture comprises at least one supplement, which is selected from the group consisting of nitric acid, hydrofluoric acid, hydrochloric acid, hydrobromic acid, methane sulphonic acid, toluene sulphonic acid, sulphamic acid, sulphuric acid and mixtures hereof.

8. The method according to claim 1, wherein after conversion, the reaction mixture is reprocessed.

9. The method according to claim 1, wherein at least one substrate which is to be coated with the adsorbent is immersed in the conversion reaction mixture as cathode together with a counter-anode and subsequently the conversion is implemented, the adsorbent being deposited on the substrate in the form of a layer, and, during conversion, a voltage being applied between the electrodes which effects a current density of 200-1,000 mA/dm$^2$ at the beginning of the conversion.

10. The method according to claim 1, wherein the substrate is a substrate made of electrically conductive ceramic, electrically conductive plastic material, copper, aluminium and/or steel.

11. The method according to claim 9, wherein the layer has a layer thickness of 120 to 180 μm.

12. The method of claim 1, wherein the sum of the proportions by percentage weight of DMSO and water in the solvent mixture is 100% by weight.

13. The method of claim 8, wherein, during said reprocessing, a solid produced during the conversion is separated from a supernatant solution.

* * * * *